(12) United States Patent
Hodgeman et al.

(10) Patent No.: US 11,798,679 B2
(45) Date of Patent: Oct. 24, 2023

(54) UNIVERSAL MEDICAL IMAGE REQUEST

(71) Applicant: MyMedicalImages.com, LLC, Boca Raton, FL (US)

(72) Inventors: John D. Hodgeman, Boca Raton, FL (US); Wayne A. Vassello, Lake Worth, FL (US)

(73) Assignee: MYMEDICALIMAGES.COM, LLC, Boca Raton, FL (US)

( * ) Notice: Subject to any disclaimer, the term of this patent is extended or adjusted under 35 U.S.C. 154(b) by 0 days.

(21) Appl. No.: 18/085,362

(22) Filed: Dec. 20, 2022

(65) Prior Publication Data

US 2023/0253096 A1    Aug. 10, 2023

Related U.S. Application Data

(60) Provisional application No. 63/308,240, filed on Feb. 9, 2022.

(51) Int. Cl.
*G16H 30/20*     (2018.01)
*G16H 40/67*     (2018.01)

(52) U.S. Cl.
CPC .............. *G16H 30/20* (2018.01); *G16H 40/67* (2018.01)

(58) Field of Classification Search
None
See application file for complete search history.

(56) References Cited

U.S. PATENT DOCUMENTS

| | | |
|---|---|---|
| 2012/0099769 A1 | 4/2012 | Eichhorn |
| 2013/0175334 A1 | 7/2013 | Miller |
| 2014/0070012 A1 | 3/2014 | Hunt et al. |
| 2014/0254796 A1 | 9/2014 | Li et al. |
| 2015/0213734 A1 | 7/2015 | Glickman |
| 2015/0358163 A1 | 12/2015 | Carter |
| 2016/0203352 A1 | 7/2016 | Marisco |

(Continued)

FOREIGN PATENT DOCUMENTS

JP        2016224793 A  * 12/2016  ............... A61B 6/03

OTHER PUBLICATIONS

Yi-Ying Chang, Huai-Bin Zhong, & Min-Liang Wang. (2014). Implementation of mobile DICOM image retrieval applicaion with QR-code authentication doi:http://dx.doi.org/10.1109/IS3C.2014.103 (Year: 2014).*

(Continued)

*Primary Examiner* — Jason S Tiedeman
*Assistant Examiner* — Emily Huynh
(74) *Attorney, Agent, or Firm* — SNELL & WILMER L.L.P.

(57) ABSTRACT

The method of obtaining DICOM files may comprise receiving, by a processor, scanning data of a scannable graphic associated with an item, wherein the scannable graphic is associated with DICOM tag data; extracting, by the processor, the DICOM tag data from the scanning data; determining, by the processor, that the DICOM tag data is associated with a first DICOM file; identifying, by the processor, a user of the first DICOM file; retrieving, by the processor, the first DICOM file; searching, by the processor, for other DICOM files that are associated with at least one of the user or the first DICOM file; retrieving, by the processor, the other DICOM files; and sending, by the processor and to the user, the first DICOM file and the other DICOM files.

19 Claims, 5 Drawing Sheets

(56) References Cited

U.S. PATENT DOCUMENTS

2019/0065763 A1* 2/2019 Berg .................. G06F 16/58
2020/0161003 A1* 5/2020 Wright ............... G16H 30/20
2021/0158933 A1* 5/2021 Frosch ............... G16H 40/67
2021/0232881 A1* 7/2021 Amir ............. G06K 19/06103
2022/0246281 A1* 8/2022 Di Grandi ........... G06T 7/0012

OTHER PUBLICATIONS

Translation (IP.com) of JP-2016224793-A. (Year: 2016).*
ISA; International Search Report and Written Opinion dated Mar. 27, 2023 in PCT/US22/53830.

* cited by examiner

UNIVERSAL MEDICAL IMAGE REQUEST

CROSS-REFERENCE TO RELATED APPLICATIONS

This application claims priority to, and the benefit of, U.S. Provisional Ser. No. 63/308,240 filed on Feb. 9, 2022 and entitled "Universal Medical Image Request", which is hereby incorporated by reference in its entirety for all purposes.

FIELD

This disclosure generally relates to requesting medical images, and more particularly, to scanning a graphic containing specified medical image DICOM tag data and other authentication data to initiate a request for a medical image.

BACKGROUND

Users (e.g., patients) may typically review their medical images with a physician as part of establishing a treatment plan and as part of the ongoing course of their treatment. The medical images are usually the result of a scan by a diagnostic device such as, for example, an X-ray device, CT scan, MRI scan, ultrasound scan, etc. This review of the images often occurs in the physician's office and the images are displayed on a monitor in the physician's office. After the review, if the user would like a copy of the images, the user needs to inform the physician, then the physician needs to inform his/her office staff. Unfortunately, such a process is often time-consuming, complicated and inefficient. After this request process (which can take days to weeks), the user is frequently asked to return to the physician's office in order to collect the images. The images are usually provided to the user on a compact disc (CD), and if the results include any type of audio, video or computer data, the results may be provided on a digital video disk (DVD). However, the CD typically contains the medical images in the Digital Imaging and Communications in Medicine (DICOM) format, so a specialized DICOM viewer is needed to view this format. The additional concern is that the industry standard for viewers does not support all computer operating systems.

User demographics and other specifics about a medical image are typically contained in a metadata section of the medical image file, commonly referred to as the DICOM tags. These tags are easily readable if the file is opened with a software application such as a DICOM file viewer or other common medical industry software applications. However, such software applications are not often readily available to users and are frequently too difficult or cumbersome to install or access on a mobile device.

Accordingly, to facilitate quick and secure exchanges of medical images between users and their physician, a need exists for a common means of obtaining specific points of data about an image. A need also exists for users to have an easier and more universal way to capture details about their medical images and to request access to those medical images.

SUMMARY

In various embodiments, the method may comprise receiving, by a processor, scanning data of a scannable graphic associated with an item, wherein the scannable graphic is associated with DICOM tag data; extracting, by the processor, the DICOM tag data from the scanning data; determining, by the processor, that the DICOM tag data is associated with a first DICOM file; identifying, by the processor, a user of the first DICOM file; retrieving, by the processor, the first DICOM file; searching, by the processor, for other DICOM files that are associated with at least one of the user or the first DICOM file; retrieving, by the processor, the other DICOM files; and sending, by the processor and to the user, the first DICOM file and the other DICOM files.

In various embodiments, the other DICOM files may be located in one or more storage devices or are located in one or more storage locations. The method may further comprise associating, by the processor, the first DICOM file with the other DICOM files. The user may include at least one of a doctor, a patient, an administrator, a person associated with the first DICOM file or an entity associated with the first DICOM file. The item may be at least one of an image, a record, an app, a photo, or a webpage. The method may further comprise sending, by the processor, the first DICOM file into a storage system associated with the user. The scannable graphic may be a QR code. The retrieving the first DICOM file may be accomplished by an image retrieval system in communication with the processor. The first DICOM file may be an electronic medical record (EMR). The method may further comprise retrieving, by the processor, the DICOM tag data associated with the item; generating, by the processor, the scannable graphic associated with the DICOM tag data; retrieving, by the processor, DICOM image data associated with the first DICOM file; associating, by the processor, the DICOM image data with the scannable graphic; and storing, by the processor, the DICOM image data and the scannable graphic. The storing the first DICOM file and the scannable graphic may include creating, by the processor, updated image data by including the scannable graphic with the first DICOM file; replacing, by the processor, the first DICOM file with updated image data; and storing, by the processor, the updated image data. The storing the updated image data may be performed by returning the updated image to the storage device via a DICOM send protocol.

In various embodiments, the associating, by the processor, the DICOM image data with the scannable graphic may include incorporating the DICOM image data into the scannable graphic. The associating, by the processor, the DICOM image data with the scannable graphic may include overlaying the scannable graphic over the DICOM image data. The associating, by the processor, the DICOM image data with the scannable graphic may include incorporating the scannable graphic into a separate window from a window that contains the DICOM image data. The associating, by the processor, the DICOM image data with the scannable graphic may include incorporating the scannable graphic into a pop-up window that is separate from a window that contains the DICOM image data.

In various embodiments, the method may comprise retrieving, by a processor, DICOM tag data associated with an item; generating, by the processor, a scannable graphic associated with the DICOM tag data; retrieving, by the processor, DICOM image data associated with a first DICOM file; associating, by the processor, the DICOM image data with the scannable graphic; and storing, by the processor, the DICOM image data and the scannable graphic.

BRIEF DESCRIPTION OF THE DRAWINGS

A more complete understanding of the present disclosure may be derived by referring to the detailed description and claims when considered in connection with the Figures, wherein like reference numbers refer to similar elements throughout the Figures, and:

DETAILED DESCRIPTION

Figure 1:
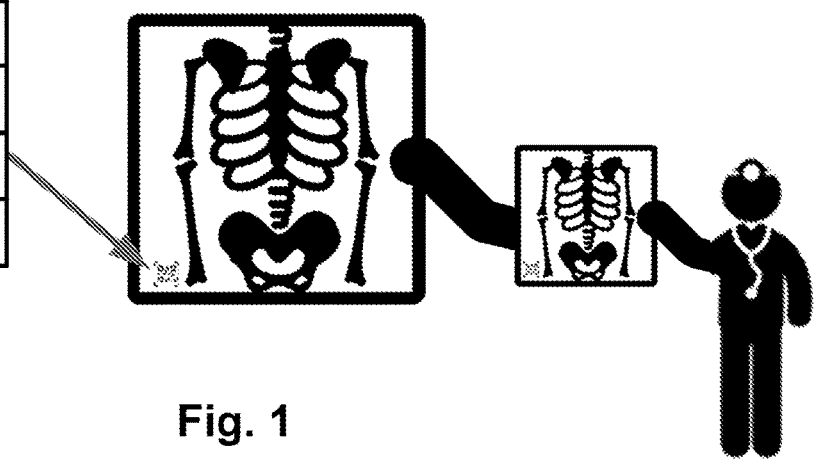
FIG. 1 is a graphical representation of a medical image with a QR code including exemplary values associated with each tag in the QR code, in accordance with various embodiments.
Figure 2:
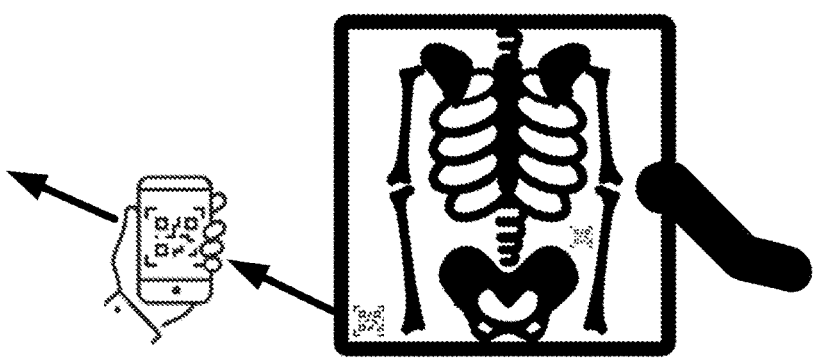
FIG. 2 is a graphical representation of a user using a smartphone to scan the QR code on the medical image to obtain the exemplary values associated with each tag in the QR code, in accordance with various embodiments.
Figure 3:
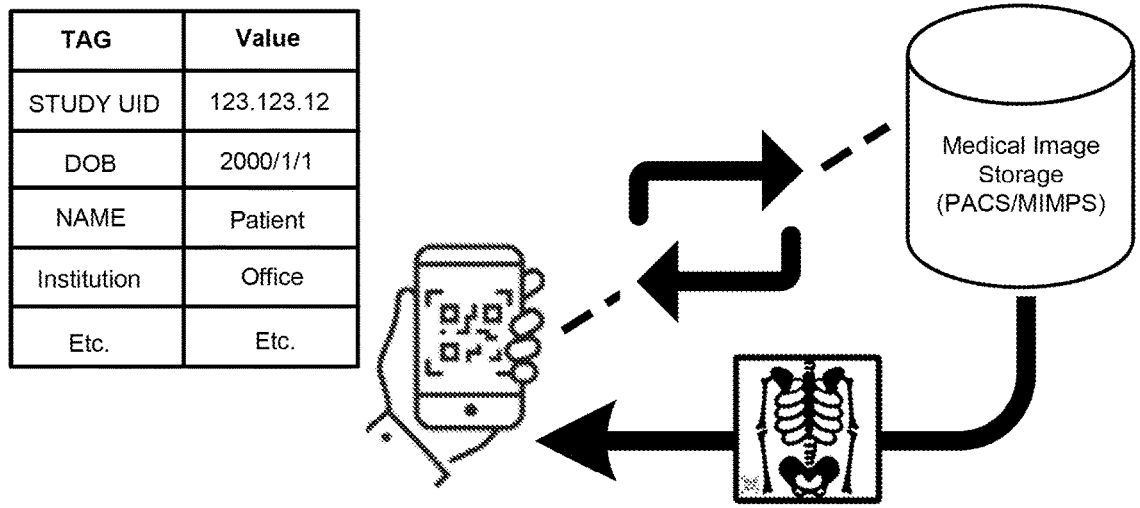
FIG. 3 is a graphical representation of a user using a smartphone to send a request data packet with the exemplary values associated with each tag to the medical image storage system, in accordance with various embodiments.

In general, in various embodiments, and as shown in FIGS. 1-3, the disclosure includes a method of creating medical image metadata associated with a medical image and allowing the metadata to be captured by a user while the medical image is displayed, typically as part of a patient-physician interaction. The system further uses the captured metadata to facilitate a request to retrieve the medical image from one or more storage systems and provide it to the user.

In various embodiments, the system may include an image, a scanning device, a medical image request system and a storage device. The medical image request system may include any device or application that gathers data and sends a request.

While this disclosure may discuss capturing metadata from a medical diagnostic image or retrieving a medical diagnostic image, the disclosure contemplates capturing metadata from any item or retrieving any item. The system may include any type of item such as, for example, an image, object, record or thing. The image may be a printed image, a scanned image, an electronic image (e.g., on a display), a 2-D image, a 3-D image, a model, replica of a body part, multiple images on one display or sheet, portions of images divided between different displays or sheets and/or the like. The record may be an electronic medical record. Moreover, the disclosure contemplates capturing metadata associated with anything such as, for example, an image, a text, an app, software, a webpage, a file, a record (e.g., electronic medical record), a database, a photo, an image, a picture, a graphic, etc. The disclosure also contemplates retrieving anything such as, for example, text, an app, software, a webpage, a file, a record (e.g., electronic medical record), a database, a photo, an image, a picture, a graphic, etc.

The images may be located in one storage device or distributed over different storage devices. As such, the system may obtain images from one or more storage devices within one facility or across many facilities. The storage device used to store the images may include any type of database or server. The storage device may include, for example, picture archiving and communication systems (PACS) or medical image management and processing systems (MIMPS). The storage device may include multiple storage devices in a distributed arrangement. The storage device may store a full image or any portion of an image. The system may acquire portions of the images from different storage devices and re-construct the full image.

As set forth in FIG. 2, in various embodiments, the scanning device used to scan the scannable graphic (e.g., QR code) may include any device that acquires data. Such scanning devices may include any type of smartphone, scanner, optical reader, recorder, video camera and/or the like.

As set forth in FIG. 1, in various embodiments, any portion or all of the metadata may be provided in any of one or more locations on the image, near the image or associated with the image. The metadata may be provided in an area that minimizes intrusion into diagnostic image. The metadata may be placed in a region outside of the diagnosing area. The scannable graphic may include the DICOM file and/or the DICOM image data. The scannable graphic may be in an overlay over the DICOM image data. The scannable graphic may be included in a separate window than the window the includes the DICOM image data. The scannable graphic may be included in a pop-up window that is a separate window than the window the includes the DICOM image data. While the metadata may be encoded in a scannable format (e.g., a QR code), the disclosure contemplates that the metadata may be provided in any format such as, for example, text, code, symbols, charts, graphs or scannable graphic. The scannable graphic may be a QR code, a bar code or any other graphic that may be scanned by a scanner.

Figure 5:
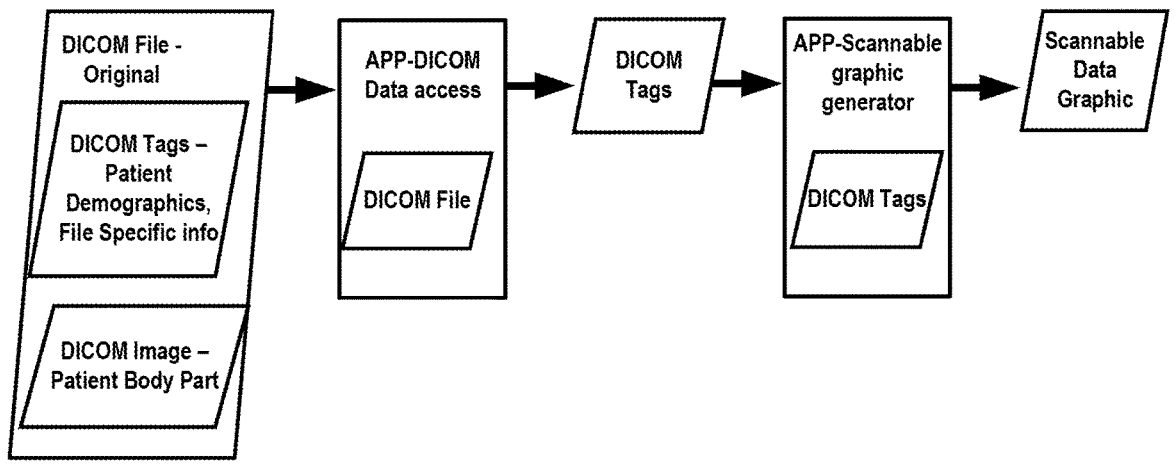
FIG. 5 is a flow diagram showing an exemplary process for generating a scannable graphic containing specified medical image DICOM tag data, in accordance with various embodiments.

In various embodiments, and as set forth in FIG. 5, the method to create a scannable graphic may comprise retrieving, by a processor, DICOM tag data associated with an item; generating, by the processor, a scannable graphic associated with the DICOM tag data; retrieving, by the processor, DICOM image data associated with a first DICOM file; associating, by the processor, the DICOM image data with the scannable graphic; and storing, by the processor, the DICOM image data and the scannable graphic. More particularly, in various embodiments, and with continued reference to FIG. 5, the system may generate a scannable graphic (e.g., QR code) containing specified medical image DICOM tag data. A formatted text file containing the DICOM tag data may be imported and/or read into a software application and/or routine within an application that is capable of creating a scannable graphic with the DICOM tag data encoded within the scannable graphic. To maintain compatibility standards, the scannable graphic may be created consistent with international standards defined in the ISO/IEC18004 standard. In various embodiments, the system may include any error correction level. The QR code may be stored into application memory and/or local data storage.

Figure 6:
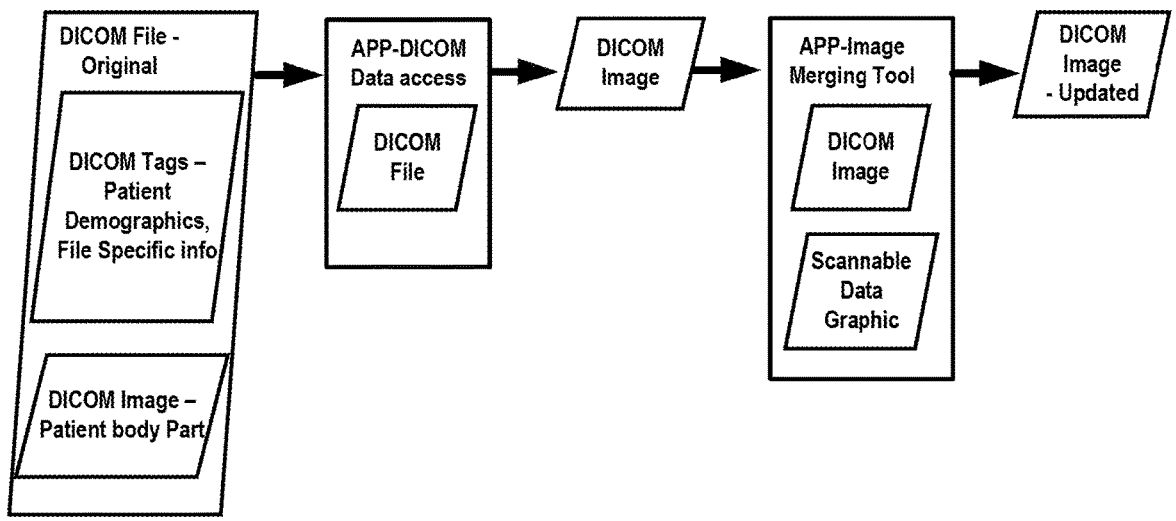
FIG. 6 is a flow diagram showing an exemplary process for retrieving DICOM image data of a specified medical image, then updating or merging the specified DICOM image data to include scannable graphic, in accordance with various embodiments.

More particularly, in various embodiments, and as set forth in FIG. 6, the system may update, associate and/or merge the specified DICOM image data with a scannable graphic. A software application and/or routine within a software application may retrieve the stored DICOM image data and may determine the image details such as, for example, size, resolution and pixel data. The software application may then retrieve the stored QR code associated with the current image file and may replace the pixel data anywhere on the DICOM image with the pixel data of the QR code. For example, the system may replace the pixel data in the lower right hand corner of the DICOM image. In various embodiments, the pixel width of the DICOM image file can be increased by the pixel width of the QR code, and the QR code data placed in the resulting image. If the DICOM image file pixel width is increased, all pixels remaining above the QR code will be blank (black). The system may center the area of concern for the user such that this region is in the center of the resulting DICOM image. The system may also place scale devices or similar additions to the DICOM image (e.g., in the lower left hand corner). Therefore, the lower right hand corner of the DICOM image may be an acceptable location to place the QR code without interfering with a physician's ability to read the image and render a diagnosis. The resulting updated DICOM image data may be stored in application memory and/or local data storage.

Figure 7:
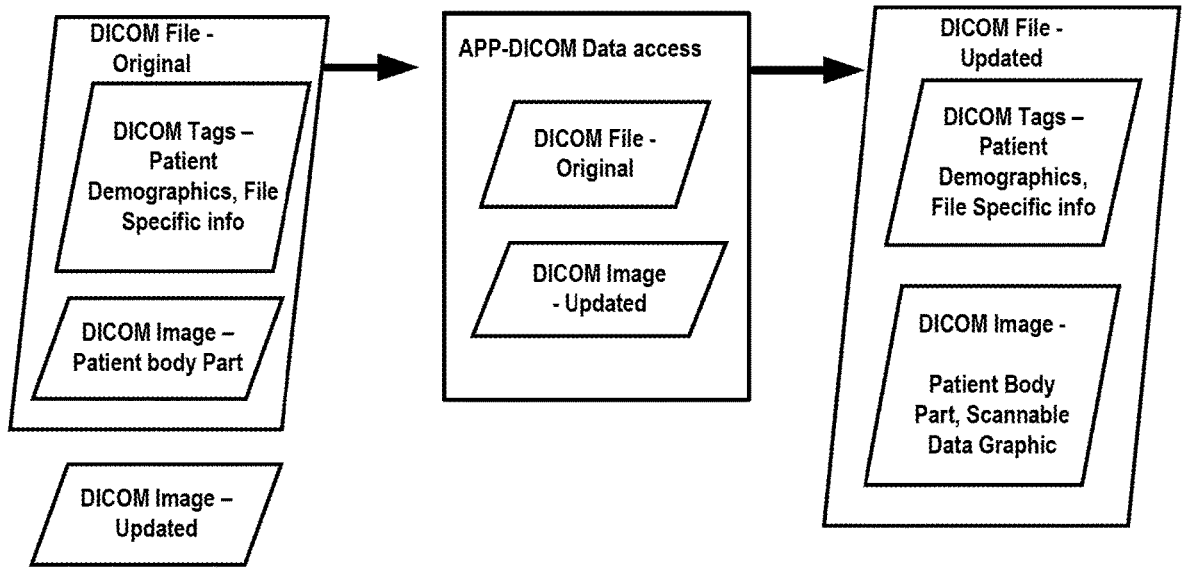
FIG. 7 is a flow diagram showing an exemplary process for replacing the original DICOM image data with updated image data, in accordance with various embodiments.

In various embodiments, and as set forth in FIG. 7, the system may replace the original DICOM image data with updated image data. The same DICOM file (or set of files) previously identified as the subject files may be imported or read by a software application and/or routine within an application that has access to commonly available libraries of DICOM file functions. The updated DICOM image data may be retrieved from memory and/or storage and written to the original DICOM data file using a DICOM file write function. The resulting updated DICOM file may be stored in application memory and/or local data storage.

In various embodiments, the system may not replace the original DICOM image data with updated image data. The system may not add to the DICOM file at all. The system may provide the DICOM image data of a specified medical image in other ways. For example, as mentioned, the system may include the DICOM image data of a specified medical image in an overlay over the image, on the screen, in an app and/or communicate such information to another system. In response to reading the DICOM image data of a specified medical image in any of these formats, the system may still retrieve the medical image(s).

In various embodiments, the updated DICOM medical image may be stored by returning the updated DICOM medical image to the PACS and/or storage solution via a DICOM send protocol. This function may be performed by a software application and/or routine within an application that has access to libraries of DICOM file functions. In various embodiments, the updated medical image may be displayed to user. In preparation for the review of the medical imaging between the physician and user, the DICOM images to be reviewed may be retrieved from the PACS and/or storage solution and displayed on a computer screen or similar monitor. The retrieval of the images from the PACS may ensure the most recent image data is displayed. The user may at that time see the updated DICOM file image data including the QR code.

Figure 4:
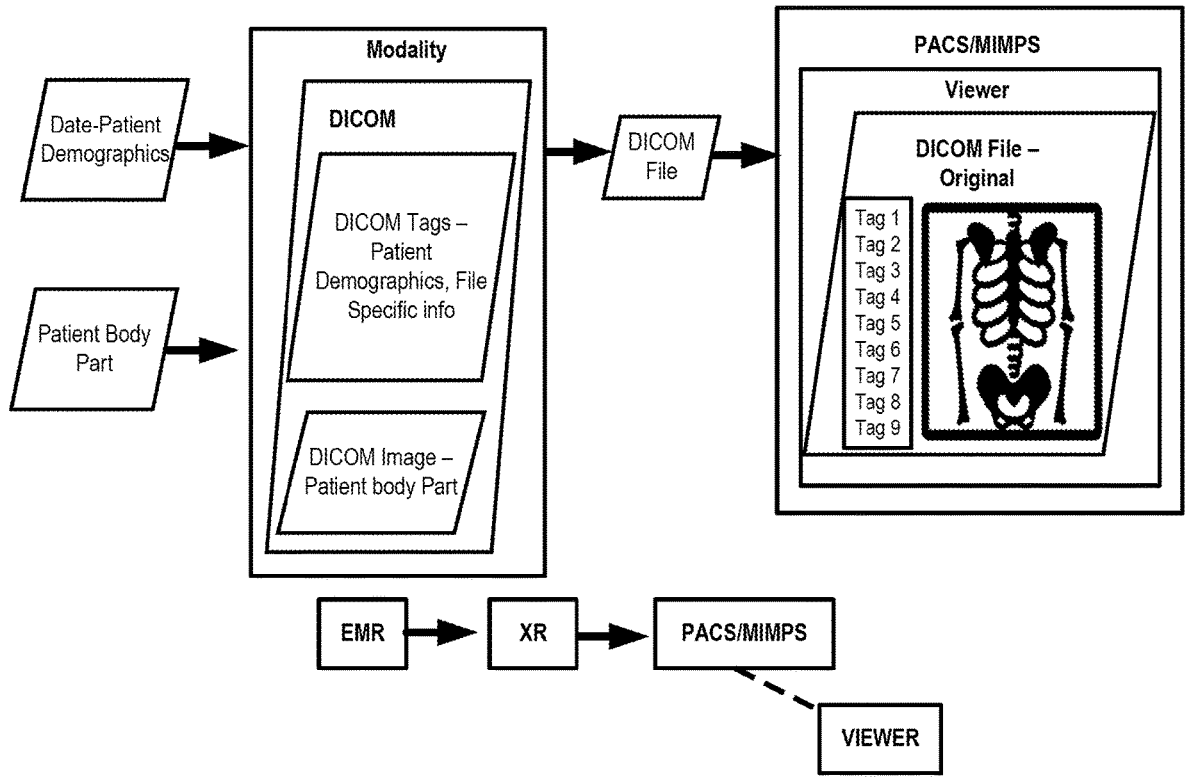
FIG. 4 is a flow diagram showing an exemplary process for retrieving DICOM tag data specific to a specified medical image, in accordance with various embodiments.

In various embodiments, and as set forth in FIG. 4, the system may retrieve a second item (e.g., DICOM files) associated with a first item (e.g., an image) by scanning a QR code associated with the first item. The QR code may include a DICOM tag data, so the scanning of the QR code captures the data from the QR code, wherein the QR code data is associated with the DICOM tag data. The system may obtain the DICOM tag data and match the DICOM tag data to a first DICOM file. The system may use the first DICOM file to identify the user of the first DICOM file. The user or requester of the items (e.g., images, DICOM file, etc) may be a doctor, a patient, an administrator, a guardian, a parent or any other person or entity associated with the DICOM file. For example, the item may be a medical diagnostic image of a patient, so user of the first DICOM file may be an image of that patient. The system may retrieve the first DICOM file. The system may look for any other DICOM files that may be associated with the user or the first DICOM file. The first DICOM file or the other DICOM files may be located in various storage devices or storage locations in the same facility or in different facilities. The system may then retrieve the other DICOM files. The system may store and/or associate the other DICOM files with the first DICOM file. The system may send the other DICOM files and the first DICOM file to the requester.

More particularly, in various embodiments and as set forth in FIG. 4, the system may retrieve DICOM tag data specific to a specified medical image. The system may retrieve the DICOM tag data in a number of ways. For example, the system may use a DICOM query command sent to a Picture Archiving and Communication System (PACS) via the DICOM protocol or via a search function within a PACS or other storage solution. The search criteria may be by known user demographics or assigned a user Medical Record Number (MRN). The DICOM file or files may be imported or read by a software application or routine within an application that has access to commonly available libraries of DICOM file functions. A particular DICOM file or set of files may be identified as the subject files associated with an image. The DICOM tags associated with the subject files are retrieved via a read function. The DICOM tag keyword, number and value for some or all of the tags may be stored in a formatted text-based file.

In various embodiments, and as set forth in FIG. 6, the system may retrieve DICOM image data of a specified medical image. The same DICOM file (or set of files) previously identified as the subject files are used to import or be read by a software application or routine within an application that has access to commonly available libraries of DICOM file functions. The DICOM image data associated with the subject file may be retrieved via a read function and stored either to application memory and/or local data storage.

Figure 8:
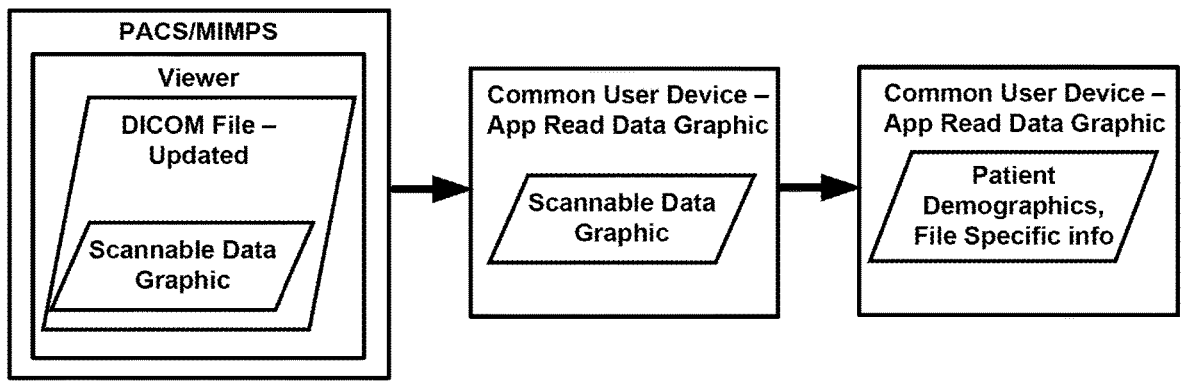
FIG. 8 is a flow diagram showing an exemplary process for allowing the user to capture the DICOM tag data through use of a common device and application, in accordance with various embodiments.

In various embodiments, and as set forth in FIG. 8, the system may allow the user to capture the DICOM tag data through the use of any device and/or application that may acquire data. During the medical imaging review, while the DICOM files are displayed on the screen, the users may use their mobile devices to scan the QR code and capture the file specific data for the image they are viewing. Since the QR code meets common standards, the scan and capture of the data can be performed by many common devices or applications. The captured data may be text based and can be stored or transmitted in a variety of ways.

Figure 9:
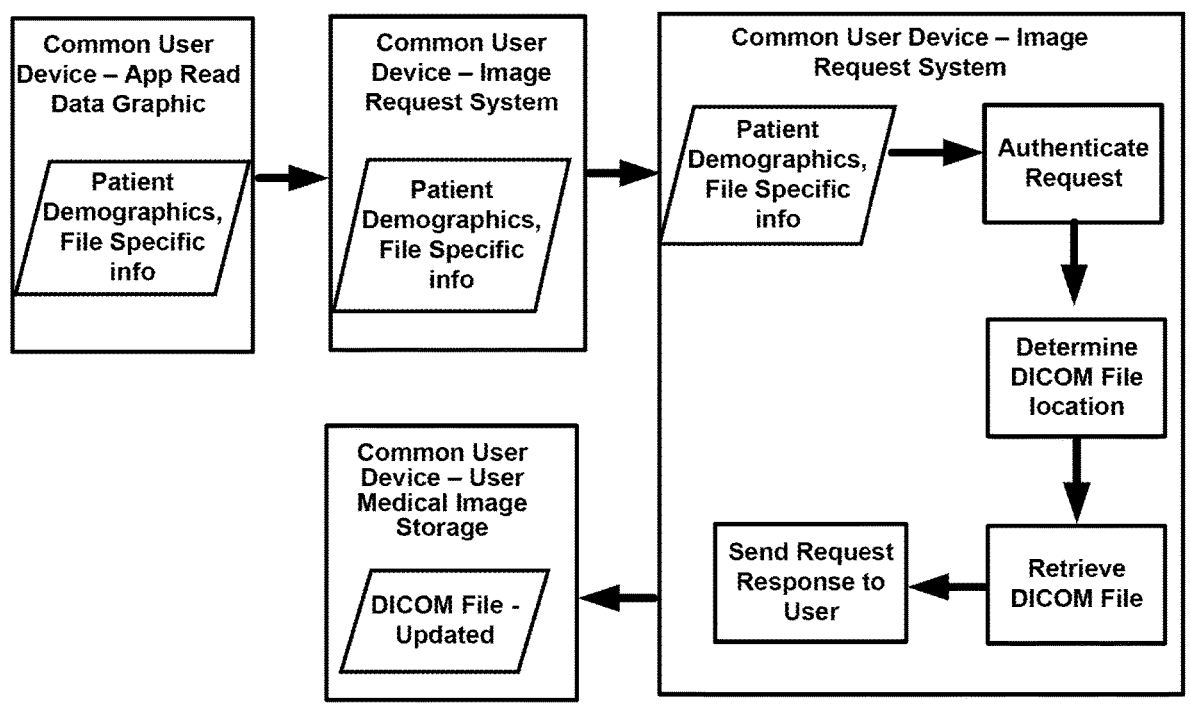
FIG. 9 is a flow diagram showing an exemplary process for submitting the DICOM tag data to a medical image request system, processing the request and locating the DICOM image file, retrieving and sending the DICOM image file to the user and sending the DICOM image file into a storage system for the user, in accordance with various embodiments.

In various embodiments, and as set forth in FIG. 9, the system may submit the DICOM tag data to a medical image request system. The user may import and/or read the captured QR Code data. The user may use a software application (and/or routine of a software application) to send the data to a medical image request system. The request may include the user's email and/or phone number as a means of identification, method of communication between the user and request system, and potentially a method to return the results of a request. In various embodiments, the user uses a software application (and/or routine of a software application) to capture the QR Code data and enter it into the application for request submission. For example, in various embodiments, the user may log into an online service, therein having a formatted form with fields which the captured data automatically populates. The form may then be submitted to the medical image request system for processing. The additional authentication information of verified email and phone may automatically be included (or selected by the user to be included) in the request.

In various embodiments, and as set forth in FIG. 9, the system may process the request and locate DICOM image file. In response to receiving a request for images, the system processes the submitted QR Code data to determine if the DICOM file specified by the QR Code data is available within the connected and associated storage solutions. The system accomplishes this by a series of lookup steps such as, for example, database queries, direct PACS queries, and/or queries of storage solutions associated with the request system. The data points used to confirm a match between the request and a DICOM file may include, for example, the user demographics and the DICOM file metadata (e.g., Study UID, SOP Instance, etc.). Additional matching data may also be used to increase the overall security of the system and for authentication of the requester. For example, if the request is received from an affiliated online service with verified user accounts, the request may need to meet an extra requirement of matching other data such as email and phone number. The format and method of receiving the request may vary. In various embodiments, the system may receive a request in the form of an email with an attached text file and/or the system may receive a request via an API interface or other direct interface.

In various embodiments, and as set forth in FIG. 9, the medical image request system may retrieve the DICOM image file and send the DICOM image file to the user. If a matching DICOM file or files is found by the medical image request system, a retrieval step may be performed to collect the files. This step can take the form of, for example, a series of DICOM file transfer commands sent to the identified PACS or storage solutions containing the files. This step copies the located files to the medical image request system storage solution. In response to all (or any subset of) specified DICOM files being located and copied to the medical image request system, the files may be sent to the requesting user via the email and/or phone (text message) provided. This send can take several forms such as, for example, an email with attached files or an included link to access the files from the medical image request system storage solution. In various embodiments, the send may take the form of an email containing a link that notifies the user requester of the available medical images with steps to create an online account with the medical image request system to enable access to the files. For circumstances where the user already has an account with the medical image request system or an affiliated online request service, the file may automatically be made available from within the user's account.

In various embodiments, and as set forth in FIG. 9, the system may send the DICOM image file into a storage system for the user. In response to receiving the email and/or text message, the user may have the option to download and/or store the DICOM files into the storage solution of their choice. This could take the form of local computer storage or commercial general online storage. In various embodiments, the user may be provided with an option for an account and online storage solution from the medical image request system. The account provided may already contain the requested images and may not require subsequent storage steps.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy," "meet," "match," "associated with", or similar phrases may include an identical match, a partial match, meeting certain criteria, matching a subset of data, a correlation, satisfying certain criteria, a correspondence, an association, an algorithmic relationship, and/or the like. Similarly, as used herein, "authenticate" or similar terms may include an exact authentication, a partial authentication, authenticating a subset of data, a correspondence, satisfying certain criteria, an association, an algorithmic relationship, and/or the like.

Terms and phrases similar to "associate" and/or "associating" may include tagging, flagging, correlating, using a look-up table or any other method or system for indicating or creating a relationship between elements, such as, for example, (i) a transaction account and (ii) an item (e.g., offer, reward, discount) and/or digital channel. Moreover, the associating may occur at any point, in response to any suitable action, event, or period of time. The associating may occur at pre-determined intervals, periodically, randomly, once, more than once, or in response to a suitable request or action. Any of the information may be distributed and/or accessed via a software enabled link, wherein the link may be sent via an email, text, post, social network input, and/or any other method known in the art.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

In various embodiments, components, modules, and/or engines of system 100 may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PUP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements.

Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

The system and method are described herein with reference to screen shots, block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

In various embodiments, the software elements of the system may also be implemented using a JAVASCRIPT® run-time environment configured to execute JAVASCRIPT® code outside of a web browser. For example, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEBSPHERE® MQ™ (formerly MQSeries) by IBM®, Inc. (Armonk, NY) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOME-POD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the embodiments are directed toward one or more computer systems capable of carrying out the functionalities described herein. The computer system includes one or more processors. The processor is connected to a communication infrastructure (e.g., a communications bus, cross-over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

The terms "computer program medium," "computer usable medium," and "computer readable medium" are used to generally refer to media such as removable storage drive and a hard disk installed in hard disk drive. These computer program products provide software to a computer system.

The computer system may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

As used herein an "identifier" may be any suitable identifier that uniquely identifies an item. For example, the identifier may be a globally unique identifier ("GUID"). The GUID may be an identifier created and/or implemented under the universally unique identifier standard. Moreover, the GUID may be stored as 128-bit value that can be displayed as 32 hexadecimal digits. The identifier may also include a major number, and a minor number. The major number and minor number may each be 16-bit integers.

In various embodiments, the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Encryption may be performed by way of any of the techniques now available in the art or which may become available—e.g., Twofish, RSA, El Gamal, Schorr signature, DSA, PGP, PKI, GPG (GnuPG), HPE Format-Preserving Encryption (FPE), Voltage, Triple DES, Blowfish, AES, MD5, HMAC, IDEA, RC6, and symmetric and asymmetric cryptosystems. The systems and methods may also incorporate SHA series cryptographic methods, elliptic curve cryptography (e.g., ECC, ECDH, ECDSA, etc.), and/or other post-quantum cryptography algorithms under development.

The firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the internet. A firewall may be integrated as software within an internet server or any other application server components, reside within another computing device, or take the form of a standalone hardware component.

Database

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, NY), various database products available from ORACLE® Corporation (Redwood Shores, CA), MICROSOFT ACCESS® or MICROSOFT SQL SERVER® by MICROSOFT® Corporation (Redmond, Washington), MYSQL® by MySQL AB (Uppsala, Sweden), MONGODB®, Redis, Apache Cassandra®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions, such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data, but instead the appropriate action may be taken by providing to the user, at the standalone device, the appropriate option for the action to be taken. The system may contemplate a data storage arrangement wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like.

Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

Any database discussed herein may comprise a distributed ledger maintained by a plurality of computing devices (e.g., nodes) over a peer-to-peer network. Each computing device maintains a copy and/or partial copy of the distributed ledger and communicates with one or more other computing devices in the network to validate and write data to the distributed ledger. The distributed ledger may use features and functionality of blockchain technology, including, for example, consensus-based validation, immutability, and cryptographically chained blocks of data. The blockchain may comprise a ledger of interconnected blocks containing data. The blockchain may provide enhanced security because each block may hold individual transactions and the results of any blockchain executables. Each block may link to the previous block and may include a timestamp. Blocks may be linked because each block may include the hash of the prior block in the blockchain. The linked blocks form a chain, with only one successor block allowed to link to one other predecessor block for a single chain. Forks may be possible where divergent chains are established from a previously uniform blockchain, though typically only one of the divergent chains will be maintained as the consensus chain. In various embodiments, the blockchain may implement smart contracts that enforce data workflows in a decentralized manner. The system may also include applications deployed on user devices such as, for example, computers, tablets, smartphones, Internet of Things devices ("IoT" devices), etc. The applications may communicate with the blockchain (e.g., directly or via a blockchain node) to transmit and retrieve data. In various embodiments, a governing organization or consortium may control access to data stored on the blockchain. Registration with the managing organization(s) may enable participation in the blockchain network.

Data transfers performed through the blockchain-based system may propagate to the connected peers within the blockchain network within a duration that may be determined by the block creation time of the specific blockchain technology implemented. For example, on an ETHEREUM®-based network, a new data entry may become available within about 13-20 seconds as of the writing. On a HYPERLEDGER® Fabric 1.0 based platform, the duration is driven by the specific consensus algorithm that is chosen, and may be performed within seconds. In that respect, propagation times in the system may be improved compared to existing systems, and implementation costs and time to market may also be drastically reduced. The system also offers increased security at least partially due to the immutable nature of data that is stored in the blockchain, reducing the probability of tampering with various data inputs and outputs. Moreover, the system may also offer increased security of data by performing cryptographic processes on the data prior to storing the data on the blockchain. Therefore, by transmitting, storing, and accessing data using the system described herein, the security of the data is improved, which decreases the risk of the computer or network from being compromised.

In various embodiments, the system may also reduce database synchronization errors by providing a common data structure, thus at least partially improving the integrity of stored data. The system also offers increased reliability and fault tolerance over traditional databases (e.g., relational databases, distributed databases, etc.) as each node operates with a full copy of the stored data, thus at least partially reducing downtime due to localized network outages and hardware failures. The system may also increase the reliability of data transfers in a network environment having reliable and unreliable peers, as each node broadcasts messages to all connected peers, and, as each block comprises a link to a previous block, a node may quickly detect a missing block and propagate a request for the missing block to the other nodes in the blockchain network.

The particular blockchain implementation described herein provides improvements over conventional technology by using a decentralized database and improved processing environments. In particular, the blockchain implementation improves computer performance by, for example, leveraging decentralized resources (e.g., lower latency). The distributed computational resources improves computer performance by, for example, reducing processing times. Furthermore, the distributed computational resources improves computer performance by improving security using, for example, cryptographic protocols.

Any communication, transmission, and/or channel discussed herein may include any system or method for delivering content (e.g., data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word or EXCEL™, an ADOBE® Portable Document Format (PDF) document, etc.), an "ebook," an "emagazine," an application or microapplication (as described herein), an short message service (SMS) or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network, and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

The invention claimed is:

1. A method comprising:
retrieving, by a processor, a formatted text file containing DICOM tag data associated with an item;
importing, by the processor, the formatted text file into a routine within a software application;
generating, by the processor using the routine within the software application, a scannable graphic that includes the DICOM tag data encoded within the scannable graphic;
retrieving, by the processor and using a software application read function and using the DICOM tag data, DICOM image data associated with a first DICOM file, wherein an application includes the software application, and wherein the application has access to accessible libraries of DICOM file functions;
determining, by the processor, size, resolution and pixel data of the DICOM image data;
increasing, by the processor, an image pixel width of the DICOM image data by a graphic pixel width of the scannable graphic;
setting, by the processor, image pixels of the DICOM image data within the increased image pixel width to black;
replacing, by the processor, a subset of the pixel data within a center portion of the DICOM image data with pixel data of the scannable graphic to form updated DICOM image data;
replacing, by the processor using a DICOM file write function, the DICOM image data with the updated DICOM image data and the scannable graphic in a memory of the software application;
receiving, by the processor, scanning data of the scannable graphic associated with the item, wherein the scannable graphic includes the DICOM tag data, wherein the DICOM tag data contains an image identifier that identifies a stored DICOM medical image;
extracting, by the processor, the DICOM tag data from the scanning data;
matching, by the processor, the image identifier with a stored image identifier contained in metadata of the first DICOM file, wherein the stored image identifier identifies the stored DICOM medical image;
determining, by the processor and based on the matching, that the DICOM tag data is associated with the first DICOM file that contains the stored image identifier that identifies the stored DICOM medical image, metadata associated with the stored DICOM medical image and the stored DICOM medical image;
verifying, by the processor, a user based on user demographics in the metadata associated with the stored DICOM medical image;
retrieving, by the processor using a DICOM read function, the first DICOM file containing the stored DICOM medical image and the metadata associated with the stored DICOM medical image;
identifying, by the processor, the user of the first DICOM file;
searching, by the processor using a DICOM query function, for other DICOM files that are associated with at least one of the user or the first DICOM file;
retrieving, by the processor using a DICOM read command, the other DICOM files;
sending, by the processor and to the user, the first DICOM file and the other DICOM files;
retrieving, by the processor and using the software application read function and using the DICOM tag data, DICOM images associated with the first DICOM file and the other DICOM files, wherein the application has access to accessible libraries of the DICOM file functions; and
transmitting, by the processor, the DICOM images to the user via at least one of an email or text from the user demographics, that includes at least one of a link to an account of the user containing the DICOM images or an attachment containing the DICOM images.

2. The method of claim 1, wherein the other DICOM files are located in one or more storage devices or are located in one or more storage locations.

3. The method of claim 1, further comprising associating, by the processor, the first DICOM file with the other DICOM files.

4. The method of claim 1, wherein the retrieving includes reading a content of the first DICOM file.

5. The method of claim 1, wherein the item is at least one of an image, a record, an app, a photo, or a webpage.

6. The method of claim 1, further comprising sending, by the processor, the first DICOM file into a storage system associated with the user.

7. The method of claim 1, wherein the scannable graphic is a QR code.

8. The method of claim 1, wherein the first DICOM file is retrieved from an image retrieval system in communication with the processor.

9. The method of claim 1, wherein the first DICOM file is an electronic medical record (EMR).

10. The method of claim 1, further comprising including, by the processor, an error correction level for the scannable graphic.

11. The method of claim 10 further comprising:
storing the updated DICOM image data and the scannable graphic by including the scannable graphic with the updated DICOM image data;
replacing, by the processor, the first DICOM file with the updated DICOM image data and the scannable graphic; and
storing, by the processor using a DICOM send protocol, the first DICOM file in a storage system.

12. The method of claim 10, wherein the replacing the updated DICOM image data is performed by returning the updated DICOM image data to the storage device via a DICOM send protocol.

13. The method of claim 10, further comprising associating, by the processor, the DICOM image data with the scannable graphic by incorporating the DICOM image data into the scannable graphic.

14. The method of claim 1, wherein the scannable graphic includes the scannable graphic overlaid over the DICOM image data.

15. The method of claim 1, wherein the scannable graphic is incorporated into a separate window from a window that contains the DICOM image data.

16. The method of claim 1, wherein the scannable graphic is incorporated into a pop-up window that is separate from a window that contains the DICOM image data.

17. A system comprising:
a processor; and
a tangible, non-transitory memory configured to communicate with the processor,
the tangible, non-transitory memory having instructions stored thereon that, in response to execution by the processor, cause the processor to perform operations comprising:
retrieving, by a processor, a formatted text file containing the DICOM tag data associated with an item;
importing, by the processor, the formatted text file into a routine within a software application;
generating, by the processor using the routine within the software application, a scannable graphic that includes the DICOM tag data encoded within the scannable graphic;
retrieving, by the processor and using a software application read function and using the DICOM tag data, DICOM image data associated with a first DICOM file, wherein an application includes the software application, and wherein the application has access to accessible libraries of DICOM file functions;
determining, by the processor, size, resolution and pixel data of the DICOM image data;
increasing, by the processor, an image pixel width of the DICOM image data by a graphic pixel width of the scannable graphic;
setting, by the processor, image pixels of the DICOM image data within the increased image pixel width to black;
replacing, by the processor, a subset of the pixel data within a center portion of the DICOM image data with pixel data of the scannable graphic to form updated DICOM image data;
replacing, by the processor using a DICOM file write function, the DICOM image data with the updated DICOM image data and the scannable graphic in a memory of the software application;
receiving, by the processor, scanning data of the scannable graphic associated with the item, wherein the scannable graphic includes the DICOM tag data, wherein the DICOM tag data contains an image identifier that identifies a stored DICOM medical image;
extracting, by the processor, the DICOM tag data from the scanning data;
matching, by the processor, the image identifier with a stored image identifier contained in metadata of the first DICOM file, wherein the stored image identifier identifies the stored DICOM medical image;
determining, by the processor and based on the matching, that the DICOM tag data is associated with the first DICOM file that contains the stored image identifier that identifies the stored DICOM medical image, metadata associated with the stored DICOM medical image and the stored DICOM medical image;
verifying, by the processor, a user based on user demographics in the metadata associated with the stored DICOM medical image;
retrieving, by the processor using a DICOM read function, the first DICOM file containing the stored DICOM medical image and the metadata associated with the stored DICOM medical image;
identifying, by the processor, the user of the first DICOM file;
searching, by the processor using a DICOM query function, for other DICOM files that are associated with at least one of the user or the first DICOM file;
retrieving, by the processor using a DICOM read command, the other DICOM files;
sending, by the processor and to the user, the first DICOM file and the other DICOM files;
retrieving, by the processor and using the software application read function and using the DICOM tag data, DICOM images associated with the first DICOM file and the other DICOM files, wherein the application has access to accessible libraries of the DICOM file functions; and
transmitting, by the processor, the DICOM images to the user via at least one of an email or text from the user demographics, that includes at least one of a link to an account of the user containing the DICOM images or an attachment containing the DICOM images.

18. The system of claim 17, wherein the item is at least one of an image, a record, an app, a photo, or a webpage.

19. The system of claim 17, wherein the scannable graphic is a QR code.

* * * * *